United States Patent
Hofmann, geb. Roth et al.

[11] Patent Number: 5,849,068
[45] Date of Patent: Dec. 15, 1998

[54] DENTAL PROSTHESIS

[75] Inventors: Carmen Hofmann, geb. Roth, Bergheim/Klessen; Ludwig J. Gauckler, Schaffhausen, both of Germany; Gerhard Bayer, Egg ZH, Australia; Martin E. Hofmann, Bergheim/Klessen; Atef Malash, Zumikon, both of Germany; Peter Schärer, Zürich; Heinz Lüthy, Neuchatel, both of Switzerland; Klaus Krumbholz; Wigbert Hauner, both of Langen, Germany; Hansjörg Janssen; Ralf Janda, both of Frankfurt am Main, Germany

[73] Assignee: Dentsply G.m.b.H., Germany

[21] Appl. No.: 846,465

[22] Filed: May 1, 1997

Related U.S. Application Data

[63] Continuation of Ser. No. 653,517, May 23, 1996, abandoned, which is a continuation of Ser. No. 432,056, Apr. 17, 1995, abandoned, which is a continuation of Ser. No. 83,137, Jun. 24, 1993, abandoned.

[51] Int. Cl.$^6$ ..................................................... C09K 3/00
[52] U.S. Cl. ....................... 106/35; 501/32; 501/103; 501/153; 501/127; 501/64; 501/65; 501/66; 501/67; 501/68; 501/69; 501/70; 501/72
[58] Field of Search ................................. 106/35; 501/32, 501/103, 127, 153, 64, 65, 66, 60, 69, 70, 72

[56] References Cited

U.S. PATENT DOCUMENTS

| | | | |
|---|---|---|---|
| Re. 32,449 | 6/1987 | Claussen et al. | 501/103 |
| 3,464,837 | 9/1969 | McLean et al. | 106/35 |
| 4,111,711 | 9/1978 | Kiehl et al. | 106/97 |
| 4,135,935 | 1/1979 | Pfeil et al. | 106/35 |
| 4,265,669 | 5/1981 | Starling et al. | 106/35 |
| 4,316,964 | 2/1982 | Lange | 501/105 |
| 4,360,598 | 11/1982 | Otagiri et al. | 501/103 |

(List continued on next page.)

FOREIGN PATENT DOCUMENTS

| | | |
|---|---|---|
| 9977910 | 9/1976 | Canada . |
| 1013775 | 7/1977 | Canada . |
| 1015778 | 8/1977 | Canada . |
| 1041557 | 10/1978 | Canada . |
| 1047756 | 2/1979 | Canada . |
| 1053408 | 5/1979 | Canada . |
| 1053709 | 5/1979 | Canada . |

(List continued on next page.)

OTHER PUBLICATIONS

Patent Abstracts of Japan, vol. 17, No. 167 (C1043) Mar. 31, 1993 –Abstract of JP–A–04 327 514 (Kyocera).

Database WPI, week 8838, Derwent Publications Ltd., London, GB; AN 88–266444 –Abstract of JP–A–63 082 653 (Kyocera); Apr. 13, 1988.

*Primary Examiner*—Melissa Bonner
*Attorney, Agent, or Firm*—Dale R. Lovercheck; James B. Bieber

[57] ABSTRACT

A shaped, high-strength dental ceramic prosthesis is made by pressing a molding composition including from about 1 to 50 percent by weight glass particles and from about 99 to about 50 percent by weight inorganic oxide particles at a pressure of from about 10 to about 40 MPa and a temperature of from about 1000° to about 1200° C. Dental prostheses prepared in accordance with the invention include crowns, bridges, inlays and onlays.

7 Claims, 1 Drawing Sheet

U.S. PATENT DOCUMENTS

| | | | |
|---|---|---|---|
| 4,415,673 | 11/1983 | Feagin | 501/102 |
| 4,426,404 | 1/1984 | Shoher et al. | 427/2 |
| 4,431,420 | 2/1984 | Adair | 433/199 |
| 4,478,641 | 10/1984 | Adair et al. | 106/110 |
| 4,504,591 | 3/1985 | Feagin | 501/102 |
| 4,506,023 | 3/1985 | Guigonis | 501/104 |
| 4,520,114 | 5/1985 | David | 501/12 |
| 4,525,464 | 6/1985 | Claussen et al. | 501/103 |
| 4,565,792 | 1/1986 | Knapp | 501/104 |
| 4,576,922 | 3/1986 | O'Brien et al. | 106/35 |
| 4,587,225 | 5/1986 | Tsukuma et al. | 501/105 |
| 4,742,030 | 5/1988 | Masaki et al. | 501/105 |
| 4,744,757 | 5/1988 | Adair et al. | 433/180 |
| 4,751,207 | 6/1988 | Manniing | 501/104 |
| 4,755,228 | 7/1988 | Sakurai et al. | 106/104 |
| 4,764,491 | 8/1988 | Quadir | 501/103 |
| 4,772,436 | 9/1988 | Tyszblat | 264/19 |
| 4,806,168 | 2/1989 | Ivarsson et al. | 106/104 |
| 4,960,733 | 10/1990 | Kasuga et al. | 501/5 |
| 4,978,640 | 12/1990 | Kelly | 501/32 |
| 5,011,673 | 4/1991 | Krechbaum et al. | 423/608 |
| 5,120,340 | 6/1992 | Ducheyne et al. | 63/18.3 |
| 5,130,210 | 7/1992 | Iwasaki et al. | 429/33 |
| 5,155,071 | 10/1992 | Jacobson | 501/103 |

FOREIGN PATENT DOCUMENTS

| | | |
|---|---|---|
| 1074341 | 3/1980 | Canada . |
| 1078412 | 5/1980 | Canada . |
| 1105498 | 7/1981 | Canada . |
| 1120960 | 3/1982 | Canada . |
| 1129688 | 8/1982 | Canada . |
| 1134869 | 11/1982 | Canada . |
| 1135728 | 11/1982 | Canada . |
| 1138155 | 12/1982 | Canada . |
| 1141396 | 2/1983 | Canada . |
| 1146980 | 5/1983 | Canada . |
| 1148306 | 6/1983 | Canada . |
| 1154793 | 10/1983 | Canada . |
| 1156679 | 11/1983 | Canada . |
| 1156684 | 11/1983 | Canada . |
| 1189092 | 6/1985 | Canada . |
| 1195702 | 10/1985 | Canada . |
| 1196032 | 10/1985 | Canada . |
| 1202333 | 3/1986 | Canada . |
| 1212125 | 9/1986 | Canada . |
| 1212302 | 10/1986 | Canada . |
| 1212970 | 10/1986 | Canada . |
| 1216007 | 12/1986 | Canada . |
| 1228372 | 10/1987 | Canada . |
| 1232620 | 2/1988 | Canada . |
| 1323619 | 2/1988 | Canada . |
| 1234163 | 3/1988 | Canada . |
| 1236855 | 3/1988 | Canada . |
| 1239656 | 7/1988 | Canada . |
| 1251305 | 3/1989 | Canada . |
| 1251306 | 3/1989 | Canada . |
| 1258557 | 8/1989 | Canada . |
| 1259079 | 9/1989 | Canada . |
| 1259507 | 9/1989 | Canada . |
| 1268490 | 5/1990 | Canada . |
| 1272222 | 7/1990 | Canada . |
| 1272491 | 8/1990 | Canada . |
| 2010595 | 8/1990 | Canada . |
| 1273648 | 9/1990 | Canada . |
| 1274857 | 10/1990 | Canada . |
| 1275185 | 10/1990 | Canada . |
| 2017884 | 11/1990 | Canada . |
| 1279154 | 1/1991 | Canada . |
| 2020486 | 1/1991 | Canada . |
| 1281340 | 3/1991 | Canada . |
| 2024646 | 3/1991 | Canada . |
| 2033289 | 6/1991 | Canada . |
| 2031666 | 7/1991 | Canada . |
| 2037343 | 8/1991 | Canada . |
| 2037372 | 9/1991 | Canada . |
| 2038695 | 9/1991 | Canada . |
| 1279154 | 11/1991 | Canada . |
| 1292017 | 11/1991 | Canada . |
| 2042349 | 11/1991 | Canada . |
| 2044041 | 12/1991 | Canada . |
| 2045859 | 1/1992 | Canada . |
| 2044060 | 2/1992 | Canada . |
| 1300178 | 5/1992 | Canada . |
| 2059402 | 7/1992 | Canada . |
| 1309845 | 11/1992 | Canada . |
| 2070691 | 12/1992 | Canada . |
| 2072946 | 1/1993 | Canada . |
| 0 161 578 | 4/1985 | European Pat. Off. . |
| 0 241 384 A2 | 4/1987 | European Pat. Off. . |
| 0 518 454 A2 | 5/1992 | European Pat. Off. . |
| 1 491 042 | 10/1964 | Germany . |
| A-2198125 | 6/1988 | United Kingdom . |

DENTAL PROSTHESIS

This is a continuation of application Ser. No. 08/653,517, filed on May 23, 1996, now abandoned, which is a continuation of application Ser. No. 08/432,056, filed on Apr. 17, 1995, now abandoned which is a continuation of application Ser. No. 08/083,137, filed on Jun. 24, 1993, now abandoned.

The invention relates to a dental prosthesis. In particular, the invention provides dental prostheses of high strength. Dental prostheses prepared according to the present invention include caps, crowns, bridges, veneers, inlays and onlays, for example, peripheral caps and crowns, bridges that are placed on stumps of natural teeth to support simultaneously the remaining parts of at least two teeth by compensating ultimately for one or more missing teeth. To produce supporting metal structure parts for dental prostheses, such as caps and frames, metal is used for its high strength, but for esthetic reasons, it is coated with a dental ceramic or acrylic veneering material to provide the form, color and contour of the dentition. The metal structure is frequently cast into a mold prepared from an inorganic investment material, but it may be formed by other methods such as computer assisted design and machining.

Most often cast metal structure is veneered with a dental ceramic or with acrylics that gives the prostheses the shape and the shade of natural teeth. The veneer material must be very opaque in order to cover the metal structure of the prosthesis which provides an undesirable appearance. Prior prostheses are not entirely bio-compatible as corrosion of the metal therein causes them to discolor and inflame adjacent gum tissue, which may also recede. Still another disadvantage is corrosion or solution effects of metal causes discoloration of the veneer or adjacent soft tissue.

A disadvantage of the prior art metal supported ceramic structures is that the metal often appears as a visible dark border at the boundary of the prosthesis in contact with the gingiva. The metal substructures are not generally completely veneered with ceramic or acrylic in this area in order to utilize the greater edge strength of metals, as well as to protect the gum against damages caused by thick margins, and as a consequence a metallic colored ring at the margin of the restoration results in less than optimal esthetic results. Another disadvantage of prosthesis which have a metal substructure is that, while the highly opaque thin coating of ceramic or acrylic obscures the influence of gray-silvery metal used to simulate the tooth color and shape, this opaque thin layer is often incompletely or inadequately applied so that the final restoration appears grayer, greener or otherwise different in shade than the adjacent natural dentition.

Claussen et al in U.S. Pat. No. Re. 32,449 discloses ceramic body of zirconium dioxide ($ZRO_2$) and method for its preparation. Lange in U.S. Pat. No. 4,316,964 discloses $Al_2O_3/ZRO_2$ ceramic. Claussen et al in U.S. Pat. No. 4,525,464 discloses ceramic body of zirconium dioxide ($ZrO_2$) and method for its preparation. Knapp in U.S. Pat. No. 4,565,792 discloses partially stabilized zirconia bodies. Tsukuma et al in U.S. Pat. No. 4,587,225 discloses high-strength zirconia type sintered body. Manniing in U.S. Pat. No. 4,751,207 discloses alumina-zirconia ceramic. Kelly in U.S. Pat. No. 4,978,640 discloses dispersion strengthened composite. Kriechbaum et al in U.S. Pat. No. 5,011,673 discloses zirconium oxide powder. Iwasaki et al in U.S. Pat. No. 5,130,210 discloses stabilized zirconia solid electrolyte and process for preparation thereof. Jacobson in U.S. Pat. No. 5,155,071 discloses flame-produced partially stabilized zirconia powder. Tyszblat in U.S. Pat. No. 4,772,436 discloses a complicated and time consuming method of preparing prosthesis from alumina. Adair and Adair et al in U.S. Pat. Nos. 4,744,757; 4,478,641 and 4,431,420 disclose glass ceramic dental products. Quadir; Masaki et al; David and Otagiai et al in U.S. Pat. Nos. 4,764,491; 4,742,030; 4,520,114 and 4,360,598 respectively disclose zirconia ceramics. Feagin, Guigonis, Sakurai et al and Ivarsson et al in U.S. Pat. Nos. 4,415,673; 4,504,591; 4,506,023; 4,755,228 and 4,806,168 respectively disclose refractory materials. Hieke et al in U.S. Pat. No. 4,111,711 discloses cements. Ducheyne et al in U.S. Pat. No. 5,120,340 discloses bioreactive material for a prosthesis. Adair in Canadian Patent 1,148,306 discloses dental products and processes involving mica compositions. Otagiri et al in Canadian Patent 1,154,793 discloses zirconia ceramic and a method of producing the same. Feagin in Canadian Patent 1,202,333 discloses refractory material. Adair et al in Canadian Patent 1,212,125 discloses embedding material useful in preparing glass-ceramic products. Ivarsson et al in Canadian Patent 1,239,656 discloses refractory material and its use. Adair et al in Canadian Patent 1,259,507 discloses fixed partial dentures and method of making. Tyszblat in Canadian Patent Application 1,309,845 discloses procedure for making a prosthesis. Duchyne et al in Canadian Patent Application 2,024,646 discloses material for prosthesis. Grebe et al in Canadian Patent Application 2,072,946 discloses rare earth-containing frits having a high glass transition temperature and their use for the production of enamels having improved heat resistance. Jones in Canadian Patent Application 2,045,859 discloses compositions. Andrus et al in Canadian Patent Application 2,044,060 discloses coated refractory article and method. Ditz et al in Canadian Patent Application 2,042,349 discloses biocompatible glass. Rheinberger et al in Canadian Patent Application 2,038,695 discloses polymerizable dental materials. Corcilium in Canadian Patent Application 2,037,343 discloses glass composition. Kubota et al in Canadian Patent Application 2,033,289 discloses alumina-zirconia composite sintered product and method for making the same. Ricoult et al in Canadian Patent Application 2,031,666 discloses transparent glass-ceramic articles. Anderson in Canadian Patent Application 2,010,595 discloses method for producing a ceramic unit. Tsukuma et al in Canadian Patent Application 1,300,178 discloses ceramic orthodontic bracket and process for making same. Akahane et al in Canadian Patent 1,292,017 discloses glass powders for dental glass ionomer cements. Manning in Canadian Patent 1,268,490 discloses alumine-zirconia ceramic. Heurtaux in Canadian Patent 1,258,557 discloses basal ceramic layer for opacifying the metal coping of a ceramo-methallic dental reconstruction. Howard in Canadian Patent 1,234,163 discloses support particles coated with precursors for biologically active glass. Manning in Canadian Patent 1,232,620 discloses alumina ceramic comprising a siliceous binder and at least one of zirconia and hafnia. Beall et al in Canadian Patent 1,196,032 discloses transparent glass ceramic containing mullite. Richez in Canadian Patent 1,195,702 discloses Material bioreactives. Potter et al in Canadian Patent 1,189,092 discloses glasses. Schmitt et al in Canadian Patent 1,156,679 discloses calcium aluminum fluorosilicate glass powder. Starling et al in Canadian Patent 1,146,980 discloses ceramic dental appliance and method and dental ceramic for the manufacture thereof. Perez in Canadian Patent 1,129,688 discloses internal ceramic core. Barrett et al in Canadian Patent 1,120,960 discloses glass-ceramic dental restorations. Gagin in Canadian Patent 1,105,498 discloses alkali-resistant glass fiber composition. Neely in Canadian Patent 1,078,412 discloses low pollution glass fiber compositions. Ohtomo in Canadian Patent 1,074,341 discloses alkali-resistant glass composition and glass fibers made therefrom. Sung in Canadian Patent 1,053,408 discloses dental bonding agents. Deeg et al in Canadian Patent 1,047,756 discloses faraday rotation glasses. Ohtomo in Canadian Patent 1,040,222 discloses alkali resistant glass. Atkinson et al in Canadian Patent 1,015,778 discloses glass compositions and fibers made therefrom. Wolf in Canadian Patent 1,013,775 discloses glass composition. Hancock et al in Canadian Patent 997,791 discloses sintered zirconia bodies. Tamamaki et al in Canadian Patent 2,059,402 discloses fused Alumina-zirconia-yttria refractory materials. Tamamaki et al in Canadian Patent 2,044,041 discloses fused zirconia refractory materials having high-temperature heat resistance and corrosion resistance and a method for producing the same. Morishita in Canadian Patent 1,281,340 discloses zirconia ceramics and a process for production thereof. Matsuo et al in Canadian Patent 1,273,648 discloses refractory material and castable refractory for molten methal container. Bush et al in Canadian Patent 1,272,491 discloses magnesia partially-stabilized zirconia. Colombet et al in Canadian Patent 1,259,079 discloses zirconia stabilizers. Guile in Canadian Patent 1,236,855 discloses stabilized zirconia bodies of improved toughness. Sugie in Canadian Patent 1,228,372 discloses process for producing a zirconia refractory body and a product produced by the process. Knapp in Canadian Patent 1,216,007 discloses partially stabilized zirconia bodies. Garvie et al in Canadian Patent 1,135,728 discloses partially stabilized zirconia ceramics. Schulz et al in Canadian Patent 1,134,869 discloses thixotropic refractory binder based upon aluminum phosphate gelled silica sols. Garvie et al in Canadian Patent 1,053,709 discloses ceramic materials. Linton in Canadian Patent 1,041,557 discloses acid and heat-resistant mortars for cellular glass. Labant et al in Canadian Patent Application 2,037,372 discloses enamel compositions. Becker in Canadian Patent Application 2,017,884 discloses glass composition. Klaus et al in Canadian Patent 1,279,154 discloses dental compositions fired dental porcelains and processes for making and using same. Bailey et al in Canadian Patent 1,275,185 discloses Bonding glass-ceramic dental products. Klimas et al in Canadian Patent 1,274,857 discloses lead-free glass frit compositions. Katz in Canadian Patent 1,272,222 discloses high strength dental porcelains. Heurtaux in Canadian Patent 1,251,306 discloses ceramic intermediate layer for a ceramo-metallic dental reconstruction. Heurtaux in Canadian Patent 1,251,305 discloses transparent ceramic surface layer for a ceramo-metallic dental reconstruction. Francel et al in Canadian Patent 1,232,619 discloses lead-free and cadmium-free glass frit compositions for glazing, enameling and decorating. Francel et al in Canadian Patent 1,212,970 discloses lead-free and cadmium-free glass frit composition for glazing, enameling and decorating. Hagy et al in Canadian patent 1,156,684 discloses very low expansion sealing frits. Eppler in Canadian Patent 1,141,396 discloses low-melting, lead-free ceramic frits. Chaung in Canadian Patent 1,212,302 discloses method for etching dental porcelain. Prall in Canadian Patent 1,138,155 discloses cordierite crystal-containing glaze. Berneburg in Canadian Patent Application 2,020,486 discloses aluminum oxide ceramic having improved mechanical properties.

It is known to use dental ceramic as replacements for metal but most often the resulting product has been too weak to fulfill the needed mechanical strength in practice, or else the procedure used has been excessively difficult and unreliable.

It is an object of the invention to provide a material and method for producing a completely non-metallic prosthesis comprising a ceramic frame material and an esthetic ceramic veneer material and methods for their manufacture.

It is an object of the invention to provide ceramic/glass dental compositions which are adapted to be molded at high pressure while heating to form prosthesis and prosthetic parts.

It is an object of the invention to provide compositions of zirconia and/or alumina powders, and glass powder which are molded to provide high strength dental prosthetic components and parts.

It is an object of the invention to provide dental prosthesis and prosthetic parts by molding compositions of zirconia or alumina powders and their mixtures with an admixture of powdered silicate and aluminosilicate glasses under heat and pressure to produce high strength prosthetic components and parts.

It is an object of the invention to provide compositions of zirconia and/or alumina powders, silicate and/or aluminosilicate glass powders, which are molded to produce high strength dental prosthetic components and parts veneered with esthetic dental ceramics.

It is an object of the invention to provide ceramic veneering materials suitable for providing esthetic ceramic coatings to the moldings of this invention.

It is the object of the invention to provide a process for forming ceramic/glass dental prosthesis and prosthetic components and parts having superior esthetic and strength properties.

It is an object of the invention to provide a process for molding dental prosthesis and prosthetic components and parts from a molding composition which includes ceramic and glass powders while heating under pressure.

It is an object of the invention to provide a process for molding zirconia and/or alumina powders and glass powder to provide high strength prosthetic components and parts.

It is an object of the invention to provide a process for molding zirconia and/or alumina powders and silicate and/or aluminosilicate glass powder to produce high strength prosthetic components and parts which are then coated with a slurry of dental ceramic, and fired.

It is the object of the invention to provide investment materials suitable for preparing molds within which the ceramic/glass compositions of the invention are molded.

It is an object of the invention to provide molding apparatus suitable for molding dental prosthesis from the ceramic/glass materials of the invention at elevated temperatures and high pressure.

It is an object of the invention to provide dental equipment suitable for molding dental prosthesis from the ceramic/glass materials of the invention at elevated temperatures and high pressure while vacuum is applied to the mold.

Mbar as used herein means millibar.

Dental prosthesis as used herein means any article of manufacture used to replace a missing element of the oral cavity, especially the hard and adjacent soft tissues, teeth and gingiva including caps, crowns, veneers, bridges, inlays, onlays, and dentures or any part thereof.

Throughout this disclosure all percentages are percent by weight unless otherwise indicated.

BRIEF DESCRIPTION OF THE INVENTION

A shaped, high-strength dental ceramic prosthesis is provided by molding a composition which includes from about 1–50 percent by weight glass particles and from 50–99 percent by weight of ceramic particles at pressures up to about 40 MPa and temperatures up to about 1200° C.

DETAILED DESCRIPTION OF THE INVENTION

The invention provides a prosthesis by molding ceramic/glass powder compositions under heat and pressure. A prosthesis is made by forming a wax or wax-substitute into a model of the shape and size of the ceramic prosthesis to be formed. This model is then surrounded with an investment material within a mold ring. The investment material is allowed to harden while being thermally conditioned. The model is physically removed or burned out of the hardened investment material at high temperature to leave a mold with a cavity having the shape and size of the dental prosthesis (molding) to be formed. The ceramic/glass molding powder composition is then transferred to the cavity and heated under pressure to produce a molded dental prosthesis.

In an embodiment of the invention vacuum is applied to the mold during molding and/or heating. The time and rate of cooling of the molded dental prosthesis in the investment material is controlled so that the molding is tempered to relieve internal stresses. The molded dental prosthesis is subsequently divested. The dental prosthesis preferably is veneered with an additional lower-temperature-forming ceramic to produce an individually characterized prosthesis with natural appearing variations in color and translucency to most aesthetically match adjacent teeth. Veneering ceramics are used which have good adhesion to the molded dental prosthesis, and approximately the same coefficient of thermal expansion. The veneering compositions are applied directly to the molded dental prosthesis as a slurry of powder and aqueous liquid, which is then fired at a temperature lower than the molding temperature of the molded dental prosthesis.

CERAMIC/GLASS MOLDING COMPOSITION

Thus, in accordance with the invention high strength dental prostheses are formed, which do not require metal substructure, by applying pressure and heat to a ceramic/glass powder composition in a mold. The ceramic/glass powder composition preferably includes alumina powder and/or zirconia powder, and a glass powder. It has been found that the addition of the glass facilitates molding highly refractory ceramic powders such as alumina and zirconia at sintering temperatures lower than the ceramic powders alone while surprisingly providing higher strength prosthesis. Preferably the ceramic powder has a melting point which is at least 1000° C. higher than the softening temperature of the glass powder. Preferably the ceramic/glass molding powder composition includes from about 50 to about 99 parts by weight alumina and/or zirconia powder and from about 1 to about 50 parts by weight of glass powder. Based upon the chemical nature of the glass, and its physical properties including softening point and viscosity, the ceramic/glass molding composition is fired at a temperature between 800° and 1300° C. To assure condensation of the ceramic/glass molding composition, pressures of up to about 40 MPa, are applied during firing. The pressure is applied for optimal condensation of the ceramic/glass composition. Preferably a vacuum is applied to the mold before and/or during firing to remove occluded air from and through the investment material, ceramic/glass molding composition and the mold cavity to assist in forming prostheses with reduced porosity and greater strength. The flexural strengths of the prostheses produced in accordance with the invention are at least greater than about 150 MPa, and more preferably greater than 300 MPa; most preferably greater than 500 MPa.

In a preferred embodiment a powdered ceramic/glass molding composition of the invention includes from about 50 to 99 parts by weight of powdered alumina and/or yttrium stabilized zirconia and 1 to 50 parts by weight of aluminosilicate glass. Preferably, components of ceramic/glass molding compositions of the invention are sufficiently mixed to substantially evenly distribute the glass and ceramic particles. More preferably the ceramic/glass molding composition includes from 60 to 85 parts by weight of powdered alumina or yttrium stabilized zirconia and 15 to 40 parts by weight of aluminosilicate glass powder. Most preferably the ceramic/glass molding composition includes from 65 to 80 parts by weight of powdered alumina or yttrium stabilized zirconia with particles sizes less than 35 microns and 20 to 35 parts by weight of aluminosilicate glass.

In another preferred embodiment of a ceramic/glass molding composition of the invention includes from about 10 to 70 parts by weight (pbw) of powdered yttrium stabilized zirconia, 10 to 70 parts by weight alumina and 1 to 50 parts by weight of lanthanum borosilicate glass powder. More preferably a ceramic/glass molding composition of the invention includes from 20 to 50 pbw of powdered yttrium stabilized zirconia, 20 to 50 pbw alumina, and 15 to 40 parts by weight of lanthanum aluminoborosilicate glass powder. Most preferably a ceramic/glass molding composition of the invention includes from 20 to 50 pbw of powdered yttrium stabilized zirconia with particles sizes less than 35 microns, 20 to 50 pbw alumina with particles less than 35 $\mu$m, and 20 to 35 parts by weight of lanthanum aluminoborosilicate glass, principally in powder form with particles less than 100 $\mu$m.

In another preferred embodiment a molding powder is prepared from 50 to 99 parts by weight of powdered alumina and/or yttrium stabilized zirconia which are overcoated with from 1 to 50 parts by weight of a silicate or aluminosilicate glass which in a preferred embodiment is a lanthanum borosilicate glass and comminuted to powder to which is than admixed 1 to 50 parts by weight of a second powdered silicate or aluminosilicate glass. In a more preferred embodiment 50 to 90 pbw alumina or yttrium stabilized zirconia are overcoated with 1 to 40 pbw lanthanum borosilicate glass and comminuted to powder to which is admixed 10 to 50 pbw of a powdered aluminosilicate glass. In a most preferred embodiment 50 to 85 pbw alumina or yttrium stabilized zirconia are overcoated with 1 to 30 pbw lanthanum borosilicate glass and comminuted to powder to which is admixed 15 to 35 pbw of a powdered aluminosilicate glass.

Preferably the average particle size of the ceramic powder of the ceramic/glass molding composition is less than 35 $\mu$m, more preferably less than 10 $\mu$m and most preferably less than 5 $\mu$m. These particles preferably have a distribution of sizes that leads to close packing.

The glass powder particles of the ceramic/glass molding composition preferably have a coefficient of thermal expansion between 3 and $15 \times 10^{-6}$ per K. at temperatures between 25 and 400° C., and an average particle size less than 100 μm, more preferably less than 35 μm and most preferably less than 5 μm. Preferably the glass of the ceramic/glass molding composition includes lanthanum, aluminum, boron, silicon, calcium, zirconia, yttrium and small amounts of other elements which readily form cations.

In a preferred embodiment of the invention a lanthanum aluminoborosilicate glass component of the glass/ceramic molding composition includes:

5 to 30 percent by weight of $SiO_2$, 5 to 25 percent by weight of $B_2O_3$, 5 to 30 percent by weight of $Al_2O_3$, 20 to 60 percent by weight of $La_2O_3$, 0 to 15 percent by weight of CaO, 0 to 15 percent by weight of $ZrO_2$, and 0 to 15 percent by weight of $Y_2O_3$.

In a more preferred embodiment of the invention the lanthanum aluminoborosilicate glass of the glass/ceramic molding composition includes:

10 to 25 percent by weight of $SiO_2$, 10 to 20 percent by weight of $B_2O_3$, 10 to 20 percent by weight of $Al_2O_3$, 30 to 50 percent by weight of $La_2O_3$, 0 to 10 percent by weight of CaO, 0 to 10 percent by weight of $ZrO_2$, and 0 to 10 percent by weight of $Y_2O_3$.

In a most preferred embodiment of the invention the lanthanum aluminoborosilicate glass of the glass/ceramic molding composition includes:

15 to 22 percent by weight of $SiO_2$, 12 to 18 percent by weight of $B_2O_3$, 14 to 20 percent by weight of $Al_2O_3$, 35 to 45 percent by weight of $La_2O_3$, 0 to 5 percent by weight of CaO, 0 to 5 percent by weight of $ZrO_2$, and 0 to 5 percent by weight of $Y_2O_3$.

Preferably a glass is of low viscosity above its softening point and is of suitable composition to optimally wet the alumina or zirconia components of the ceramic/glass molding compositions. It is believed the glass acts as a plasticizer and lubricant allowing the alumina and/or zirconia powders to surprisingly allow the composition to be substantially compressed at relatively low temperatures of less than about 1200° C. and pressures less than about 40 MPa, and thus to be molded to form high strength prosthesis of irregular shape.

In another embodiment of the invention, whereby glass and ceramic powders are mixed and molded directly at the herein before mentioned temperature and pressures it has been found that high strength ceramic particles of zirconia and alumina may be first advantageously over-coated with a minor portion of a glass of the type herein before described capable of wetting the ceramic particles by fusing with the glass and then comminuting to form a powder. The powder so formed is then mixed with a second portion of particulate glass powder of the same composition, or alternatively another silicate or aluminosilicate glass soluble with the first, by which means the molding of the composition is facilitated. In an embodiment thereof a second glass is an aluminosilicate glass which in a preferred embodiment has the following compositional ranges:

|  | Percent by weight |
|---|---|
| $SiO_2$ | 65–69 |
| $Al_2O_3$ | 9–12 |
| $K_2O$ | 7–10 |
| $Na_2O$ | 6–9 |
| $LiO_2$ | 1–2 |
| CaO | 2–4 |
| BaO | 0–1 |
| F | 0–1 |
| $CeO_2$ | 0–.5 |

After molding, the glass phase of the molded prosthesis is preferably conditioned with acids or alkali to obtain a microretentive etching pattern so that adhesive bonding to a tooth with a luting cement or composite is achieved. Likewise the ceramic/glass molding is preferably treated with well known silanes, for example, 3-methacryloyloxpropyltrimethoxy silane to provide an interactive surface with luting composites to assist in bonding the prosthesis to the luting cement or luting composite.

INVESTMENT MATERIAL COMPOSITIONS

According to the invention investment materials are provided which are of suitable high strength and physical characteristics to withstand the required molding pressures and temperatures and have coefficients of thermal expansion corresponding to that of the molded composition to allow the hot molded prosthesis to cool to a high strength article without "freezing in" excessive differential stresses that might crack or spall the article. Accordingly, in a preferred embodiment of the invention the coefficient of thermal expansion of the investment material is between $3 \times 10^{-6}$ and $15 \times 10^{-6}$ per K more preferably between $4 \times 10^{-6}$ and $13 \times 10^{-6}$ per K, and most preferably $5 \times 10^{-6}$ and $12 \times 10^{-6}$ per K between 25° and 1100° C.

The compressive strength of the investment material must be greater than the applied force upon the molding material applied by the apparatus at the molding temperature. Preferably the compressive strength is greater than about at least 15 MPa. Higher strengths at the molding temperature will allow greater pressures to be used in molding the ceramic/glass composition. For convenience in molding and for greatest accuracy the change in dimension in the investment upon hardening around the wax model, whether due to thermal effects or chemical changes, is preferably less than 2%.

In one embodiment of the invention investment material compositions are prepared from a powder and a liquid which are mixed at the time the mold is to be prepared, under vacuum, for about a minute until a homogeneous mass is obtained. Preferably 100 g powder are mixed with from 5 to about 50 parts by weight of liquid, more preferably 10 to 30 ml liquid, and most preferably 15 to 20 ml liquid. The liquid includes aqueous silica sol preferably having from 5 to 60 percent by weight silica. More preferably the aqueous silica sol has from 20 to 50 percent by weight silica. Most preferably the aqueous silica sol has from 25 to 45 percent by weight silica. The powder preferably includes a filler, either calcium or magnesium stabilized zirconia, magnesium oxide, quartz, cristobalite, fused silica, alumina and calcium fluoride or blends thereof. Optionally, the powder includes a binder for the filler which includes magnesia and mono- or diammonium hydrogen phosphate or magnesium hydrogen phosphate or blends thereof. Fillers are selected to obtain high compressive strength and coefficient of thermal expansion substantially equal to that of the ceramic/glass molding composition. In one embodiment of the invention calcium stabilized zirconia is preferred because a partial phase transformation at high temperatures reduces the shrinkage of the investment material.

A binder is preferably added to adjust the coefficient of thermal expansion and increase green strength. Preferably such binder has a weight ratio of magnesia to phosphates of from 0.5:1.5 to 1.5:0.5, and more preferably about 1:2. Preferably from 0 to 15 percent by weight of glass/ceramic powder composition is binder, and more preferably the binder is from 1 to 10 percent by weight.

PREPARATION OF THE MOLD

A metal mold ring, of size appropriate for the part to be molded, is lined with a layer of refractory felt saturated with water and is placed on a work surface. The model wax-up of the part to be molded is placed within the ring and partially embedded in newly mixed investment material. A layer of petroleum jelly, nail polish or other separator is applied to the surface of the mold when the investment is sufficiently hard that it can support the weight of a second mix poured over the surface. Hardening may require up to about 2 hours depending on the composition. A second mix is then poured against the surface of the first. Heat is then applied to the mold to remove water. At first the heat is applied slowly and carefully to allow the water to evaporate without causing cracks in the investment. Later more heat is applied so that the wax-up and other organic materials burn completely. The investment temperature is raised again, to about 1000° to 1300° C. for 30–90 minutes to strengthen the investment. A controlled cool-down cycle may be necessary to prevent cracking. Thereafter the mold is opened and the parting surfaces of the mold are coated with a refractory separating agent. In one preferred embodiment a thin layer of graphite is applied from a organic liquid (acetone) dispersion thereof as a separating agent.

FILLING THE MOLD

The amount of ceramic/glass powder molding composition required to form the molded dental prosthesis is determined by weighing the model wax-up. The weight of ceramic/glass powder molding composition required to fill the mold corresponds to the weight of the wax-up material. A conversion chart or table is preferably prepared by converting weight of wax-up material to the corresponding number of grams of molding powder composition, based upon the specific gravities of both materials. The mold cavity is charged with the amount of ceramic/glass molding composition corresponding to the amount of wax, (the chart is conveniently used for this determination) required for the molded prosthesis, and preferably a predetermined excess of ceramic/glass molding composition is added to the mold cavity.

The lower half of the mold is charged with ceramic/glass molding powder composition or optionally a water based slurry thereof and the halves brought together, and then is placed into the molding apparatus upon the platten of the pressure ram. In one preferred embodiment the molding composition is compressed while being heated, under vacuum applied to the mold, for the requisite time and temperature to form the molded prosthesis or prosthetic part.

MOLDING

In accordance with the invention molding of the ceramic/glass powder composition is carried out in a device that can apply the necessary molding forces at high temperature. Pressures of up to about 40 MPa are preferred since the ceramic/glass composition can be highly viscous even at elevated molding temperatures. In one embodiment of the invention of the ceramic/glass powder composition a vacuum is optionally applied within the mold and mold cavity to facilitate packing, remove water vapor, and to reduce air that might otherwise mix with the molten glass composition and cause increased porosity in the finished molding. Preferably, this vacuum applied within the mold cavity is up to about 20 mbar and more preferably up to about 40 mbar.

MOLDING APPARATUS

FIGS. 1–4 show a press system 10 in accordance with the invention having an optional press ring 12 circumscribing mold 14. Mold 14 has upper and lower mold halves 16 and 18 respectively each made of investment material and positioned within press ring 12. Above mold 14 is counter pressure body 20 which is made either of a ceramic, for example aluminum oxide or high strength metal. The mold 14 is supported on top of the round table 22 inside a vacuum-firing chamber exterior wall 24. Round table 22 is adapted to be lifted by a rod 26 toward counter pressure body 20 and press against press top 28.

Figure 1:
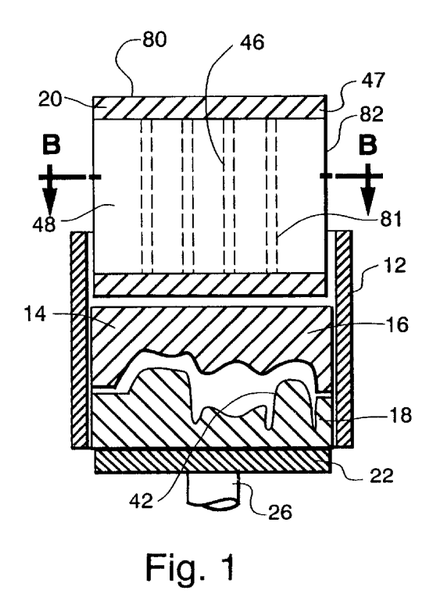
FIG. 1 is a partial side view of a press for use in making prostheses in accordance with the invention.
Figure 2:
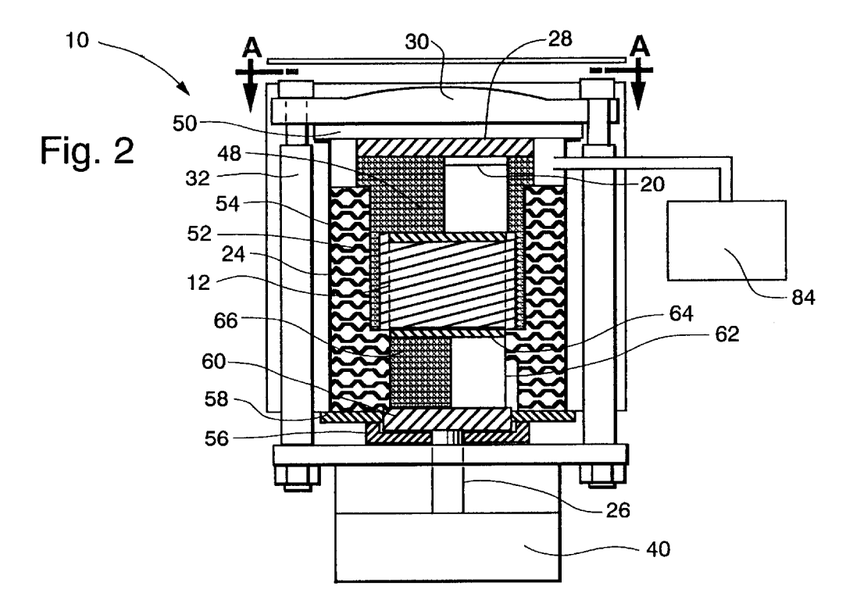
FIG. 2 is a side view of a press for use in making prostheses in accordance with the invention.

With more particular reference to FIG. 2, it is seen that press system 10 has movable cross-head 30, columns 32, and hydraulic pressure unit 40. Hydraulic unit 40 provides force on mold 14 through rod 26. The force from hydraulic unit 40 is transmitted through rod 26 onto table 22. The mold 14 contains ceramic/glass powder and is positioned within chamber exterior wall 24. Mold 14, has a mold cavity within wall 42. Removable counter-support 20 includes a high strength metal member 46 and end plattens 47, and is circumscribed by a low thermal diffusivity member 48 which is made of insulating material, such as aluminum oxide fiber or a light weight silica refractory brick. In FIG. 1 the metal members are rods passing through the refractory brick.

Mold 14 is enclosed by vacuum-firing chamber lid 50 and vacuum chamber wall 24 which when in contact with flange 56 form a seal so that a vacuum may be drawn within the chamber formed thereby. Heating elements 52 are positioned adjacent to mold 14, and within insulating material 54. Chamber wall 24 is supported by flange 56 fitted with a gasket 58. Flange 56 is connected to hydraulic unit 40. Pressure ram 60 is connected to hydraulic pressure unit 40 by means of rod 26 and extends through flange 56.

Figure 3:
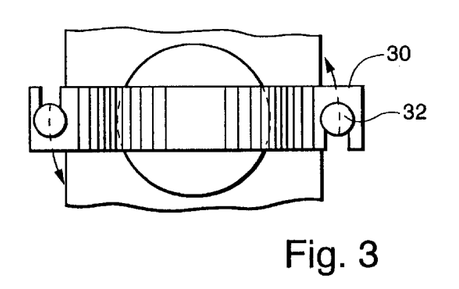
FIG. 3 is a partial top view along line A—A in FIG. 2 of a press for use in making prostheses in accordance with the invention.
Figure 4:
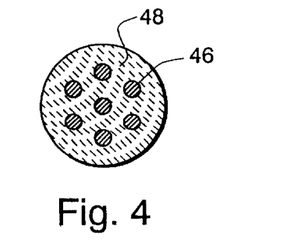
FIG. 4 is a partial cross-sectional top view along line B—B in FIG. 1 of a press for use in making prostheses in accordance with the invention.

Crosshead 30 is adapted to rotate as shown in FIG. 3, to allow removal of the vacuum-firing chamber lid 50. Pressure to close the mold is supplied through a pedestal 62 which is removably connected to pressure ram 60. Pedestal 62 includes a high strength member 64 surrounded by insulation 66. The pressure required to close and compress the contents of the mold is resisted by a counter-support 80 which includes a high strength metal member 81 surrounded by insulation 82. Vacuum is drawn by vacuum pump 84 through the vacuum-firing chamber lid 50. After molding crosshead 30 is rotated, vacuum-firing chamber lid 50 and counter support 68 are removed to permit access to the mold 14.

Alternative configurations are possible and will be obvious to those skilled in the art. For example, and not limited hereto, the motive powder to activate the pressure ram may be derived using pneumatic, hydraulic or mechanical elements such as a pneumatic cylinder, hydraulic cylinder, or threaded spindle. Likewise, the molding operation might comprise transfer or injection molding techniques alone or in combination with the compression molding technique described above.

VENEERING THE CERAMIC/GLASS PROSTHESIS

Although the prosthesis and prosthetic parts formed using the compositions of this invention are not silvery-gray and thus are themselves superior in esthetics to metal substructures, their esthetic character may be desirably enhanced in certain cases, as for example, the replacement of an anterior tooth, where the apparent color must closely approximate that of the adjacent teeth. Thus powdered ceramic compositions of superior translucency are colored to approximate natural tooth colors, and applied to a molded dental prosthesis to veneer its surface. Such veneer compositions must wet the molded dental prosthesis and have coefficients of expansion substantially equal to the coefficient of thermal expansion of the prosthesis to minimize internal stresses.

According to one embodiment of the invention the ceramic/glass part is veneered using shaded dental feldspathic ceramic powder compositions or other ceramic compositions slurried with water or a water solution of salts or polymers and painted or otherwise applied to the part to be veneered by methods known in the art, and fired in an oven at temperatures less than the molding temperatures of the ceramic/glass part. A high strength laminar composite is formed which is without cracks and checks and is resistant to breakage. To achieve these results ceramic materials have coefficients of thermal expansion similar to the substrate of ceramic/glass material. Thus in a preferred embodiment the veneering composition has coefficients of thermal expansion between $3 \times 10^{-6}$ and $13 \times 10^{-6}$ per K, more preferably between $4 \times 10^{-6}$ and $12 \times 10^{-6}$ per K and most preferably between $6 \times 10^{-6}$ and $10 \times 10^{-6}$ per K. Average particles sizes are preferable within the range of 1–40 $\mu$m, more preferable 5–35 $\mu$m, and most preferable 10–30 microns.

Ceramic powders suitable for use as veneering materials may be prepared from a single frit or combinations of two or more frits. In a preferred embodiment thereof, ceramic frits of two different coefficients of expansion are provided, such that the powdered frits can be combined in various proportions to match the coefficient of thermal expansion of the ceramic/glass part, also known as the substrate.

In a preferred embodiment of the invention at least two frits are combined to form a ceramic. One such frit (Frit I) preferably includes:

65 to 75 percent by weight of $SiO_2$,
10 to 16 percent by weight of $Al_2O_3$,
7 to 11 percent by weight of $K_2O$,
2 to 5 percent by weight of $Na_2O$,
0 to 2 percent by weight of $Li_2O$,
1 to 4 percent by weight CaO,
0 to 2 percent by weight of $B_2O_3$,
0.5 to 1 percent by weight of $Tb_2O_3$, and
0.1 to 0.3 percent by weight of $CeO_2$. More preferably such frit includes:
67 to 71 percent by weight of $SiO_2$,
12 to 15 percent by weight of $Al_2O_3$,
8 to 10 percent by weight of $K_2O$,
3 to 5 percent by weight of $Na_2O$,
0 to 1 percent by weight of $Li_2O$,
1 to 3 percent by weight of CaO,
0 to 1 percent by weight of $B_2O_3$,
0.5 to 1 percent by weight of $Tb_2O_3$, and
0.1 to 0.3 percent by weight of $CeO_2$. Another such frit (Frit II) preferably includes:
67 to 77 percent by weight of $SiO_2$,
8 to 12 percent by weight of $Al_2O_3$,
6 to 10 percent by weight of $K_2O$,
2 to 5 percent by weight of $Na_2O$,
0 to 2 percent by weight of $Li_2O$,
1 to 4 percent by weight CaO, and
1 to 4 percent by weight of $B_2O_3$. More preferably such frit includes:
70 to 75 percent by weight of $SiO_2$,
9 to 11 percent by weight of $Al_2O_3$,
8 to 10 percent by weight of $K_2O$,
2 to 4 percent by weight of $Na_2O$,
0 to 1 percent by weight of $Li_2O$,
1 to 3 percent by weight of CaO, and
2 to 3 percent by weight of $B_2O_3$. These ranges of composition of veneering ceramics frits I and II are combined to form a ceramic of suitable properties for veneering the ceramic/glass substrate. The coefficient of thermal expansion of frit I is about $8 \times 10^{-6}$ per K and the coefficient of thermal expansion of frit II is about $6.7 \times 10^{-6}$ per K.

Veneering ceramics are fired in conventional furnaces by conventional means using for example a Multimat MCII furnace (Dentsply Gmbh) in 2–5 minutes under vacuum. Firing ranges are 900°–1100° C., preferably 950°–1050° C., most preferably 980°–1020° C. The ceramics may be shaded with pigments used in the ceramic industry for example $SnO_2$, $ZrSiO_4$, Zn—Fe—Cr—Al (Spinel), and Zr—Si—Pr (Zircon). These veneering ceramics have flexural strengths greater than 50 MPa and solubility less than 0.05, values which comply with ISO 6872.

The invention is illustrated by several examples. It should be understood that these examples are not intended to limit the scope of the invention, but to be illustrative only.

EXAMPLE 1

Preparation of Investment Material

An investment material is formulated from a powder and a liquid, and used to prepare the molds in which the ceramic/glass molding compositions of Examples 3 through 7, 9 and 10 are molded. The powder component is comprised of 1.0 gram magnesium oxide, 1.0 gram ammonium monophosphate and 98.0 grams of calcium stabilized zirconium oxide ($ZrO_2$—CaO 95/5, Lonza Gmbh, Germany) which has particle sized less than 100 $\mu$m and has the following chemical composition:

|        | Percent by Weight |
|--------|-------------------|
| $ZrO_2$  | 93.8              |
| CaO    | 5.0               |
| MgO    | <0.1              |
| $SiO_2$  | <0.4              |
| $Al_2O_3$ | <0.4              |
| $Fe_2O_3$ | <0.1              |
| $TiO_2$  | <0.2              |

The liquid component is an aqueous silica sol (Lewasil 200, 30% Bayer AG, Germany). The sol is 30 percent by weight of silica. A model of wax (wax-up) of the dental prosthesis to be molded is prepared. A mold ring is placed on a work surface. A 1 mm thick lining of refractory felt (Kaoliner, Dentsply Gmbh) saturated with water is placed within the ring. 100 g powder and 17 ml liquid investment material are mixed under vacuum for about 1 minute until a homogeneous mass is obtained. A portion of newly mixed investment material, sufficient for embedding half the model (wax-up) of the object to be molded is poured into the mold and allowed to stand until it hardens. This requires approximately 60 minutes. The surface of the hardened investment material is coated with a petroleum jelly as a separating medium upon which newly mixed investment material is poured to fill the mold ring and allowed to harden. After 5 hours the mold is heated in an oven as follows: 300° C. at a rate of 4° C. per minute, then maintained at 300° C. for 0.5 hours, then heated to 1100° C. at a rate of 9° C. per minute, and then maintained at that temperature for 1 hour. The process removes water, burns out the model wax, controls shrinkage to 1% and strengthens the investment material into a mold. The investment material of the mold has a thermal expansion of $8.8 \times 10^{-6}$ per ° C. and shrinkage upon sintering of less than 1%, and a compressive strength of greater than 25 MPa.

EXAMPLE 2

MOLDING PROCEDURE

The mold formed in Example 1 is allowed to cool to room temperature and opened to reveal the mold cavity. A separating agent in the form of a slurry of graphite powder (Leit-C nach Goecke, Neubauer Chemikalien) is applied to the parting surfaces and cavity of the mold.

The quantity of ceramic/glass molding powder composition required to fill the mold is determined from the weight of the wax up, and placed into the lower half of the prepared mold. The upper mold half is placed on top of the lower half of the mold, and both halves are placed within the vacuum chamber of the press system described herein above and shown in FIGS. 1–4. The counter pressure support, the firing chamber lid, and then the rotatable crossmember are put in position to lock the assembly. 40(+/−20) mbar vacuum is applied, and the mold heated to a temperature of 1100(+/−50)° C. at a rate of 15°–20° C. per minute at which temperature a pressure of 25 MPa gauge pressure is applied. This temperature and pressure are maintained for from 25 to 30 minutes. The mold and the molded dental prosthesis therein are cooled to 800° C. at a rate of 10°–15° C. per minute, after which they are cooled to 600° C. at a rate of 1° C. per minute during which time the composition of the dental prosthesis is tempered to optimize strength. Following this the mold is cooled to 200° C. at a rate of 10°–15° C. per minute, whereupon the press system is opened to remove the mold and divest the dental prosthesis. Any investment material clinging to the dental prosthesis is removed by sandblasting.

EXAMPLE 3

PREPARATION OF DENTAL PROSTHESIS FROM A COMPOSITION OF ZIRCONIA AND GLASS 90 g of zirconium dioxide powder is mixed with 10 g of lanthanum boroaluminosilicate glass powder to form a ceramic/glass molding powder composition. The zirconium dioxide powder used to make the ceramic/glass molding powder composition is tetragonal zirconia polycrystals stabilized with 5% by weight of yttrium oxide (Tosoh Corporation Tokyo, Japan) having a crystal size of 26 nanometer (nm) and a coefficient of thermal expansion of $10 \times 10^{-6}$ per K and an average particle size of from 0.1 to 5 μm. The glass powder used to make the ceramic/glass molding powder composition is a lanthanum aluminoborosilicate glass having a coefficient of thermal expansion of $6.2 \times 10^{-6}$ per K and an average particle size less than 5 μm, and has the following chemical composition:

|  | Percent by weight |
|---|---|
| $SiO_2$ | 18.4 |
| $B_2O_3$ | 14.3 |
| $Al_2O_3$ | 16.4 |
| $La_2O_3$ | 40.9 |
| CaO | 2.8 |
| $ZrO_2$ | 4.1 |
| $Y_2O_3$ | 3.1 |

This ceramic/glass composition is put in a mold (made of investment material as described in Example 1). The mold with the ceramic/glass composition therein is positioned within a press system as described in Example 2 and then heated to 1100° C. This temperature is maintained for 30 minutes while a pressure of 25 MPa and a vacuum of 40 mbar are applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. which avoids the creation of tension at the glass transition temperature. Following this tempering they are cooled from 600° to 200° C. at a rate of 10°–15° C. per minute. They are then removed from the press system and the mold is divested from the dental prosthesis. The dental prosthesis has a flexural strength of 470 MPa when tested according to ISO 6872.

EXAMPLE 4

PREPARATION OF DENTAL PROSTHESIS FROM A COMPOSITION OF ZIRCONIA AND GLASS 80 g of the zirconium dioxide powder (used in Example 3) is mixed with 20 g of the lanthanum boroaluminosilicate glass powder (used in Example 3) to form a ceramic/glass composition. This ceramic/glass composition is put in a mold (made of investment material as described in Example 1). The mold with the ceramic/glass composition therein is positioned within a press system as described in Example 2 and then heated to 1100° C. This temperature is maintained for 30 minutes while a pressure of 25 MPa and a vacuum of 40 mbar are applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. which avoids the creation of tension at the glass transition temperature. Following this tempering they are cooled from, 600° to 200° C. at a rate of 10°–15° C. per minute. They are then removed from the press system and the mold is divested from the dental prosthesis. The dental prosthesis has a flexural strength of 550 MPa when tested according to ISO 6872.

EXAMPLE 5

PREPARATION OF DENTAL PROSTHESIS FROM A COMPOSITION OF ZIRCONIA AND GLASS 75 g of the zirconium dioxide powder (used in Example 3) is mixed with 25 g of the lanthanum boroaluminosilicate glass powder (used in Example 3) to form a ceramic/glass composition. This ceramic/glass composition is put in a mold (made of investment material as described in Example 1). The mold with the ceramic/glass composition therein is positioned within a press system as described in Example 2 and then heated to 1100° C. This temperature is maintained for 30 minutes while a pressure of 25 MPa and a vacuum of 40 mbar are applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. which avoids the creation of tension at the glass transition temperature. Following this tempering they are cooled from, 600° to 200° C. at a rate of 10°–15° C./per minute. They are then removed from the press system and the mold is divested from the dental prosthesis. The dental prosthesis has a flexural strength of 620 MPa when tested according to ISO 6872.

EXAMPLE 6

PREPARATION OF DENTAL PROSTHESIS FROM A COMPOSITION OF ZIRCONIA AND GLASS 70 g of the zirconium dioxide powder (used in Example 3) is intimately mixed with 30 g of the lanthanum boroaluminosilicate glass powder (used in Example 3) to form a ceramic/glass composition. This ceramic/glass composition is put in a mold (made of investment material as described in Example 1). The mold with the ceramic/glass composition therein is positioned within a press system as described in Example 2 and then heated to 1100° C. This temperature is maintained for 30 minutes while a pressure of 25 MPa and a vacuum of 40 mbar are applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. which avoids the creation of tension at the glass transition temperature. Following this tempering they are cooled from, 600° to 200° C. at a rate of 10°–15° C. per minute. They are then removed from the press system and the mold is divested from the dental prosthesis. The dental prosthesis has a flexural strength of 600 MPa when tested according to ISO 6872.

EXAMPLE 7

PREPARATION OF DENTAL PROSTHESIS FROM A COMPOSITION OF ZIRCONIA AND GLASS 60 g of the zirconium dioxide powder (used in Example 3 ) is intimately mixed with 40 g of the lanthanum boroaluminosilicate glass powder (used in Example 3 ) to form a ceramic/glass composition. This ceramic/glass composition is put in a mold (made of investment material as described in Example 1). The mold with the ceramic/glass composition therein is positioned within a press system as described in Example 2 and then heated to 1100° C. This temperature is maintained for 30 minutes while a pressure of 25 MPa and a vacuum of 40 mbar are applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. which avoids the creation of tension at the glass transition temperature. Following this tempering they are cooled from, 600° to 200° C. at a rate of 10°–15° C./per minute. They are then removed from the press system and the mold is divested from the dental prosthesis. The dental prosthesis has a flexural strength of 300 MPa when tested according to ISO 6872. This composition, containing 40% glass, molded easily although its strength was somewhat less than 3, 4, 5 and 6. Thus, it is believed that an optimum formulation exists for each formulation of ceramic/glass molding powder.

EXAMPLE 8

PREPARATION OF DENTAL PROSTHESIS FROM A COMPOSITION OF ALUMINA AND GLASS 70 g of alumina powder (Alcoa Chemical and Minerals Inc. Type A-16 which is 99.7% pure alpha alumina with a surface area of 9 square meters per gram and a crystal size of 0.03–3.5 μm) is mixed with 30 g of lanthanum boroaluminosilicate glass powder of Example 2 to form a ceramic/glass composition. This ceramic/glass composition is put in a mold (made of investment material as described in Example 11). The mold with the ceramic/glass composition therein is positioned within a press system as described in Example 2 and then heated to 1100° C. No vacuum is drawn upon the mold. This temperature is maintained for 30 minutes while a pressure of 25 MPa is applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. (which avoids the creation of tension at the glass transition temperature). Following this tempering they are cooled from, 600° to 200° C. at a rate of 10°–15° C./per minute. They are then removed from the press system and the mold is divested from the dental prosthesis. The dental prosthesis has a flexural strength of 300 MPa when tested according to ISO 6872.

EXAMPLE 9

PREPARATION OF DENTAL PROSTHESIS FROM A COMPOSITION OF ZIRCONIA, ALUMINA AND GLASS 56 g of the zirconium dioxide powder (used in Example 3) is mixed with 14 g alumina powder (Alcoa Chemical and Minerals Inc. Type A-16 which is 99.7% pure alpha alumina with a surface area of 9 square meters per gram and a crystal size of 0.03–3.5 μm) and 30 g of the lanthanum boroaluminosilicate glass powder (used in Example 3) to form a ceramic/glass composition. This ceramic/glass composition is put in a mold (made of investment material as described in Example 1). The mold with the ceramic/glass composition therein is positioned within a press system as described in Example 2 and then heated to 1100° C. This temperature is maintained for 30 minutes while a pressure of 25 MPa is applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. (which avoids the creation of tension at the glass transition temperature). Following this tempering they are cooled from, 600° to 200° C. at a rate of 10°–15° C./per minute. They are then removed from the press system and the mold is divested from the dental prosthesis. The dental prosthesis has a flexural strength of 600 MPa when tested according to ISO 6872.

EXAMPLE 10

PREPARATION OF DENTAL PROSTHESIS FROM A COMPOSITION OF ZIRCONIA, ALUMINA AND GLASS 42 g of the zirconium dioxide powder (used in Example 3) is mixed with 28 g of alumina powder (Alcoa Chemical and Minerals Inc. Type A-16 which is 99.7% pure alpha alumina with a surface area of 9 square meters per gram and a crystal size of 0.03–3.5 μm) 30 g of lanthanum boroaluminosilicate glass powder of Example 2 to form a ceramic/glass composition. This ceramic/glass composition is put in a mold (made of investment material as described in Example 11). The mold with the ceramic/glass composition therein is positioned within a press system as described in Example 2 and then heated to 1100° C. This temperature is maintained for 30 minutes while a pressure of 25 MPa and a vacuum of 40 mbar are applied to the mold to form a molded dental prosthesis. The mold and molded dental prosthesis therein are then cooled to 800° C. at a rate of 10°–15° C. per minute. Then they are cooled at a tempering rate of 1° C. per minute from 800° to 600° C. (which avoids the creation of tension at the glass transition temperature). Following this tempering they are cooled from, 600° to 200° C. at a rate of 10°–15° C./per minute. They are then removed from the press system and the mold is divested from the dental prosthesis. The dental prosthesis has a flexural strength of 600 MPa when tested according to ISO 6872.

The flexural strength of the dental prosthesis of Example 9 and 10 is surprisingly greater than the dental prosthesis formed in Example 8 which has a flexural strength of 300 MPa.

Investment material made as described in Example 11 is used to prepare molds in which the ceramic glass molding composition of Example 8 is molded. The investment material of Example 11 exhibits a lower coefficient of thermal expansion than the investment material of Example 1.

EXAMPLE 11

INVESTMENT MATERIAL

Investment material is prepared by mixing 1.0 part by weight of magnesium oxide, 1.0 part by weight of monoammonium phosphate, and 98.0 parts by weight of magnesium stabilized zirconium oxide ($ZrO_2$—MgO 94/6, Lonza Gmbh, Germany) powder with particle sizes less than 100 μm and which has the following chemical composition:

|  | Percent by Weight |
| --- | --- |
| $ZrO_2$ and $HFO_2$ | 93.5 |
| MgO | 6.0 |
| $SiO_2$ | less than 0.4 |
| CaO | less than 0.2 |
| $Al_2O_3$ | less than 0.2 |
| $Fe_2O_3$ | less than 0.1 |
| $TiO_2$ | less than 0.2 |

This powder mixture is intimately mixed together and combined with 17 ml of aqueous silica sol (Lewasil 200, 30% Bayer AG, Germany), which includes 30 percent by weight of silica. This mixing is done under vacuum for about of 1 minute until a homogeneous mass of investment material is obtained. The hardened investment material has a coefficient of thermal expansion of 5.0 $10^{-6}$ per K and shrinkage upon sintering of less than 1%. The investment material has a compressive strength of greater than 25 MPa.

EXAMPLE 12

VENEERING DENTAL PROSTHESIS

A molded dental bridge made by the procedure of Example 5 has a coefficient of thermal expansion about 6.5×10$^{-6}$ per K. A coating of veneering ceramic powder having the following composition is applied to the bridge.

|  | Percent by weight |
| --- | --- |
| $SiO_2$ | 73.8 |
| $Al_2O_3$ | 10.4 |
| $K_2O$ | 8.3 |
| $Na_2O$ | 4.0 |
| CaO | 1.2 |
| $B_2O_3$ | 2.3 |

The veneering ceramic powder has a median particle size of 18 μm. It is mixed together with suitable pigments and opacifiers to give the desired tooth shade. The mixture is applied to the surface of the substructure from a slurry in water. The coefficient of thermal expansion of the veneering ceramic is 6.7×10$^{-6}$ per K and its flexural strength and acid solubility are 66 MPa and 0.02% respectively determined according to ISO Standard 6872. The veneer powder coated dental bridge is fired at a temperature of 1000° C. to form a veneered dental bridge without the formation of cracks or any other visually detectable evidence of failure.

EXAMPLE 13

VENEERING DENTAL PROSTHESIS

A molded dental bridge made by the procedure of Example 10 has a coefficient of thermal expansion about 8.05×10$^{-6}$ per K. A coating of veneering ceramic powder having the following composition is applied to the bridge.

|  | Percent by Weight |
| --- | --- |
| $SiO_2$ | 68.9 |
| $Al_2O_3$ | 14.5 |
| $K_2O$ | 8.6 |
| $Na_2O$ | 4.3 |
| CaO | 1.8 |
| $Li_2O$ | 0.8 |
| $Tb_2O_3$ | 0.8 |
| $CeO_2$ | 0.2 |

The veneering ceramic powder has a particle size of 18 μm and after addition of pigment is applied to the surface of the molded dental bridge as an aqueous slurry. This coated bridge is fired at 1000° C. to form a veneered dental bridge without formation of cracks or other visually detectable evidence of failure. The coefficient of thermal expansion of the veneering ceramic is 7.9×10$^{-6}$ per K. Its solubility is 0.01% in acid and its flexural strength is 78 MPa as determined according to ISO Standard 6872.

TABLE 1

| Ceramic-glass compositions and products of Examples 3–10. | | | | | | | | |
| --- | --- | --- | --- | --- | --- | --- | --- | --- |
| Example | 3 | 4 | 5 | 6 | 7 | 8 | 9 | 10 |
| Composition (Percent by weight) | | | | | | | | |
| Zirconia $ZrO_2$ | 90 | 80 | 75 | 70 | 60 | 0 | 56 | 42 |
| Alumina $Al_2O_3$ | 0 | 0 | 0 | 0 | 0 | 70 | 14 | 28 |
| lanthanum aluminoboro | 10 | 20 | 25 | 30 | 40 | 30 | 30 | 30 |

TABLE 1-continued

Ceramic-glass compositions and products of Examples 3–10.

| Example | 3 | 4 | 5 | 6 | 7 | 8 | 9 | 10 |
|---|---|---|---|---|---|---|---|---|
| silicate glass |  |  |  |  |  |  |  |  |
| Physical property of product |  |  |  |  |  |  |  |  |
| Flexural strength [MPa] | 470 | 550 | 620 | 600 | 300 | 300 | 600 | 600 |

EXAMPLE 14

INVESTMENT MATERIAL

An investment material is prepared by mixing 100 g of ceramic powder with particle sizes less than 100 µm, having the following chemical composition:

|  | Percent by Weight |
|---|---|
| Ca-stabilized Zirconia | 50 |
| Quartz | 20 |
| Christobalite | 9 |
| Fused Silica | 15 |
| Magnesium Oxide | 2.25 |
| Monoammoniumhydrogenphosphate | 2.25 |
| Magnesium Phosphate | 1.50 | with 19 ml of aqueous silica sol containing 35 percent by weight of silica. This mixing is done under vacuum for about of 1 minute until a homogeneous mass of investment material is obtained. This investment material has a coefficient of thermal expansion of $11 \times 10^{-6}$ per K.

EXAMPLE 15

MOLD MAKING PROCEDURE

A model of wax (wax-up) of the dental prosthesis to be molded is prepared. A mold ring (as shown in FIG. 1 at 40) is placed on a work surface. A 1 mm thick lining of refractory felt (Kaoliner, Dentsply Gmbh) saturated with water is placed within the ring. A portion of newly mixed investment material prepared as described in Example 14 in an amount, sufficient for embedding half the model (wax-up) of the dental prosthesis to be molded is poured into the mold and allowed to stand until it hardens. This requires approximately 30 minutes. The surface of the hardened investment material is coated with a petroleum jelly as a separating medium upon which newly mixed investment material is poured to fill the mold ring and allowed to harden. After approximately 1 hour, the mold is opened. The wax up is physically removed and the cavity of the mold is filled with the ceramic/glass powder composition of Example 16.

EXAMPLE 16

PREPARATION OF DENTAL PROSTHESIS FROM POWDER COMPOSITION OF ZIRCONIA AND GLASS 97 g zirconia (3Y-TZP) is blended with 3 g lanthanum boroaluminosilicate glass of Example 2 and sintered for one hour at 1100° C. After cooling the sintered material is milled into a powder having a particle size of less than 10 µm. Then this powder is mixed with 20 g of a glass with the following composition:

|  | Percent by Weight |
|---|---|
| $SiO_2$ | 66.7 |
| $Al_2O_3$ | 10.5 |
| $K_2O$ | 8.3 |
| $Na_2O$ | 7.4 |
| $Li_2O$ | 1.8 |
| CaO | 3.2 |
| BaO | 0.9 |
| $CeO_2$ | 0.5 |
| F | 0.7 |

This ceramic/glass composition is put in a mold (made by the procedure as described in Example 15). The mold with the ceramic/glass composition therein is positioned within a press system as described in Example 2 and then heated to 120° C. for 1 hour to ensure the evaporation of the water and then heated to and then held at 1100° C. This temperature is maintained for 30 minutes while a pressure of 25 MPa is applied to the mold to form a molded dental prosthesis. The mold and molded dental prosthesis therein are then cooled to 800° C. at a rate of 10°–15° C. per minute. Then they are cooled at a tempering rate of 1° C. per minute from 800° C. to 600° C. (which avoids the creation of tension at the glass transition temperature). Following this tempering they are cooled from 600° C. to 200° C. at a rate of 10°–15° C./per minute. They are then removed from the press system and the mold is divested from the dental prosthesis. The coefficient of thermal expansion of the molded composition is $10 \times 10^{-6}$ per K.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A shaped, high-strength dental prosthesis, comprising a prosthesis body formed by molding, and then pressing and heating a ceramic molding composition, said molding composition comprising from 1 to 50 parts by weight of glass particles, said glass comprising oxides of silicon, aluminum, lanthanum, zirconium, boron, calcium and yttrium, and from 50 to 99 parts by weight ceramic particles, said pressing being at about 25 MPa and at temperatures between about 800° to 1300° C., said prosthesis having a flexural strength of at least about 300 MPa when tested according to ISO 6872.

2. A shaped, high-strength dental prosthesis, comprising a prosthesis body formed by molding, heating and pressing a ceramic molding composition, said molding composition comprising from 1 to 50 parts by weight of lanthanum aluminoborosilicate glass particles and from 50 to 99 parts by weight ceramic particles, said pressing being at about 25 MPa and at temperatures between about 800° to 1300° C., said prosthesis having a flexural strength of at least about 300 MPa when tested according to ISO 6872.

3. A shaped, high-strength dental prosthesis, comprising: a prosthesis body formed by molding, heating and pressing a ceramic molding composition, said molding composition comprising from 1 to 50 parts by weight glass particles and from 50 to 99 parts by weight ceramic particles, said ceramic particles comprising at least one of zirconia and alumina, said ceramic particles are coated with a minor proportion of a first glass and comminuted to a powder, said first glass being a lanthanum aluminoborosilicate glass, said powder then admixed with a second glass powder to form said molding composition, said molding composition is molded, and then pressed to pressures of about 25 MPa and at temperatures between about 800° to 1300° C. to form said prosthesis, said prosthesis having a flexural strength of at least about 300 MPa when tested according to ISO 6872.

4. A shaped, high-strength dental prosthesis, comprising a prosthesis body formed by molding, and then heating, pressing and applying vacuum to a ceramic molding composition, said molding composition comprising from 1 to 50 parts by weight glass particles and from 50 to 99 parts by weight ceramic particles, said pressing being to pressures of about 25 MPa and at temperatures between about 800° to 1300° C., said glass comprising oxides of silicon, aluminum, lanthanum, zirconia, boron, calcium and yttrium said prosthesis having a flexural strength of at least 300 MPa.

5. A shaped, high-strength dental prosthesis, comprising a prosthesis body formed by molding and heating a ceramic molding composition, said molding composition comprising from 1 to 50 parts by weight glass particles and from 50 to 99 parts by weight ceramic particles, said heating being at temperatures between about 800° to 1300° C., said glass comprising oxides of silicon, aluminum, lanthanum, zirconia, boron, calcium and yttrium.

6. A shaped, high-strength dental prosthesis, comprising a prosthesis body formed by molding and heating a ceramic molding composition, said molding composition comprising from 1 to 50 parts by weight lanthanum aluminoborosilicate glass particles and from 50 to 99 parts by weight ceramic particles, said heating being at temperatures between about 800° to 1300° C.

7. A shaped, high-strength dental prosthesis, comprising: a prosthesis body formed by molding, and then heating, pressing and applying vacuum to a ceramic molding composition, said molding composition comprising from 1 to 50 parts by weight glass particles and from 50 to 99 parts by weight ceramic particles, said ceramic particles comprising at least one of zirconia and alumina, said ceramic particles are coated with a minor proportion of a first glass and comminuted to a powder, said powder then admixed with a second glass powder to form said molding composition, said molding composition is molded, and then pressed to pressures of about 25 MPa at temperatures between about 800° to 1300° C. to form said prosthesis, said prosthesis having a flexural strength of at least about 300 MPa said first glass being a lanthanum aluminoborosilicate glass.

* * * * *